United States Patent [19]

Hydes et al.

[11] 4,225,529
[45] Sep. 30, 1980

[54] COMPOSITIONS CONTAINING PLATINUM

[75] Inventors: Paul C. Hydes; Bernard W. Malerbi, both of Reading, England

[73] Assignee: Johnson, Matthey & Co., Limited, London, England

[21] Appl. No.: 952,982

[22] Filed: Oct. 17, 1978

[30] Foreign Application Priority Data

Oct. 19, 1977 [GB] United Kingdom ............... 43491/77
May 18, 1978 [GB] United Kingdom ............... 20463/78
Jul. 12, 1978 [GB] United Kingdom ............... 29630/78

[51] Int. Cl.² ............................................. C07F 15/00
[52] U.S. Cl. .............................................. 260/429 R
[58] Field of Search ................................... 260/429 R

[56] References Cited

U.S. PATENT DOCUMENTS

| | | | |
|---|---|---|---|
| 3,892,790 | 7/1975 | Tobe et al. | 260/429 R |
| 3,904,663 | 9/1975 | Tobe et al. | 260/429 R |
| 4,115,418 | 9/1978 | Gale et al. | 260/429 R |
| 4,140,707 | 2/1979 | Cleare et al. | 260/429 R |

OTHER PUBLICATIONS

Cleare et al., Platinum Metal Rev., 17, pp. 4, 8, 11, (1973).
Leh et al., J. Pharmaceutical Sciences, 60, (3), pp. 315-320, (1976).
Cleare et al., Bioinorganic Chemistry, 2, pp. 191, 196, 199, (1973).
Meischen et al., J. Natl. Cancer Inst., 57, (4), pp. 841-845, (1976).
Tobe et al., J. of Clinical Hematology and Oncology, vol. 7, No. 1, pp. 116, 127, 131, (1971).

*Primary Examiner*—Helen M. S. Sneed
*Attorney, Agent, or Firm*—Cushman, Darby & Cushman

[57] ABSTRACT

A cis co-ordination compound of platinum having the structure

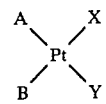

in which X and Y are the same or different ligands selected from halide, sulphate, phosphate, nitrate, carboxylate, carboxylate substituted with halogen and water and A and B are the same or different straight-chain alkyl amines containing at least 3 carbon atoms in the alkyl chain co-ordinated to the Pt through their N atoms, such that the platinum is present as $Pt^{2+}$.

4 Claims, No Drawings

COMPOSITIONS CONTAINING PLATINUM

This invention relates to new platinum co-ordination compounds and to pharmaceutical compositions containing them.

According to a first aspect of the present invention, a composition of matter comprises a cis co-ordination compound of platinum having the structure

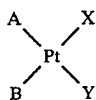

in which X and Y are the same or different ligands selected from halide, sulphate, phosphate, nitrate, carboxylate, substituted carboxylate and water and A and B are the same or different straight-chain amines co-ordinated to the Pt through their N atoms, such that the platinum is present as $Pt^2$. By phosphate we mean both $H_2PO_4^-$ and $HPO_4^{2-}$.

Where X and/or Y is represented by carboxylate or substituted carboxylate, the general formula of which is $C_nR_{2n+1}CO_2H$, that n is an integer from 1 to 9 inclusive and that the B groups are the same or different and are selected from hydrogen, substituted or unsubstituted straight- or branched-chain alkyl, arly, alkaryl, aralkyl, alkenyl, cycloalkyl and cycloalkenyl, halogen, pseudohalogen, hydroxy, carbonyl, formyl, nitro, amido, amino, alkoxy, aryloxy and sulphonic acid salts. We intend the above definition also to include oxygen and sulphur, such that one doubly-bonded oxygen or sulphur atom is represented by two R groups.

Where X and Y are both carboxylate, they can together comprise a discarboxylate bidentate ligand, for example oxalate and ligands having the general formula

where $n^1$ is an integer from 2 to 6, $R^1$ and $R^2$ are the same or different and are selected from H, lower alkyl, aryl, alkaryl, aralkyl, alkenyl, cycloalkyl, cycloalkenyl, alkoxy, aryloxy, halogen, pseudohalogen, OH, or are combined with the carbon atoms to form a cycloalkyl or an aryl group, and substituted derivatives thereof, and y and z are either 0 or 1 as long as (y+z) is equal to 1 or 2.

Suitable dicarboxylate ligands are the succinato, glutarato (pentanedioato), adipato (hexanedioato), pimelato (heptanedioate) malaro (cis-butenedioato) and phthalato (o-benzenedicarboxylate) ligands and these may be either substituted or unsubstituted.

The ligands may contain substituents selected from the group consisting of lower alkyl, (e.g. methyl, ethyl, n-propyl, isopropyl, n-butyl); aryl (e.g. phenyl, lower alkyl-, lower alkenyl-, halo-, nitro-, lower alkoxy-substituted phenyl and naphthyl) aralkyl, (e.g. phenymethyl(benzyl), 2-(1-naphthyl) methyl); alkenyl, (e.g. 4-amino-1-butene, allyl); cyclo-alkyl, (e.g. cyclopropyl, cyclohexyl); cyclo-alkenyl, (e.g. 2-cyclopenten-1-yl), 2-cyclo-hexen-1-yl); alkoxy; (e.g. methoxy, ethoxy), and hydroxy.

The straight chain amine has the general formula:

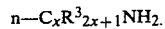

in which x is an integer from 1 to 9 inclusive and the $R^3$ groups are the same or different and are selected from hydrogen, aryl, cycloalkyl and cycloalkenyl, aralkyl, halogen, pseudohalogen (as hereinafter defined), hydroxy, alkoxy, aryloxy, carbonyl, formyl, nitro, amido, amino, acylamino, sulphonic acid, sulphonic acid salt, carboxylic acid ester and carboxylic acid salt. Even more preferably all the $R^3$ groups are hydrogen. However, where one or more of the $R^3$ groups is other than hydrogen, it can be a solubilising group, for example a sulphonic acid, carboxylic acid, carboxylic acid salt or a sulphonic acid salt. Where a solubilising group is used in the form of a salt, the salt can be, for example, the sodium, potassium or lithium salt, where conditions are appropriate and the clinical conditions require high solubility. We intend the above definition of $R^3$ also to include oxygen and sulphur, such that one doubly-bonded oxygen or sulphur atom is represented by two $R^3$ groups.

The term "pseudohalogen" in this specification has the meaning given on p. 560 of "Advanced Inorganic Chemistry" by Cotton and Wilkinson, Interscience Publishers, 1966, as being "a molecule consisting of more than two electronegative atoms which, in the free state, resembles the halogens; these pseudohalogens give rise to anions which resemble the halide ions in behaviour". Examples of suitable pseudohalogenides are cyanide, cyanate, thiocyanate and azide.

The term "cis" as applied to the compounds of the invention indicates that the compounds have planar structure and that A cannot be in a position trans to B and that X cannot be in a position trans to Y.

Two particular compounds according to the invention are cis dichloro di-n-propylamine Pt (II) and cis dichloro-di-n-butylamine Pt(II).

Normally the compound is used in association with a pharmaceutically acceptable carrier therefore. Accordingly, in a second aspect, the present invention provides a pharmaceutical composition which comprises a compound according to the first aspect of the invention and a pharmaceutically-acceptable carrier for said compound; these compositions can be formulated so as to be suitable, for example, for parenteral or oral administration to animals.

PREPARATION OF COMPLEXES ACCORDING TO THE INVENTION

The following Examples describe some specific preparations of compounds according to the invention.

Examples 1, 2 and 3 describe the preparation of compounds formed by reaction of cis-[$PtI_2A_2$] with $AgNO_3$ and throughout the remainder of this specification such compounds will be referred to as "diaquo compounds". In each case, the cis-[$PtI_2A_2$] may be prepared by the method of S. C. Dhara described in the Indian Journal of Chemistry, 8, 143 (1970).

EXAMPLE 1

Preparation of the n-butylamine diaquo complex cis-[$PtI_2(n-C_4H_9NH_2)_2$] (120 g, 0.20 mol) was slurried with a warm solution of silver nitrate (66 g, 0.38 mol) in water (200 ml). The mixture was stirred for 3 hours during which time the yellow suspension turned pale grey. The mixture was then treated with charcoal, stirred and filtered through a porosity 4 sinter. The residue was washed once with 30 ml of water and the washings were combined with the filtrate (total volume 300 ml). The addition of a crystal of sodium chloride gave no precipitate of AgCl which indicated that the solution was silver free. The solution was treated with charcoal and filtered through a porosity 4 sinter immediately before use since there was a tendency for the pale yellow solution to darken owing to slow decomposition to platinum.

EXAMPLE 2

Preparation of the n-propylamine diaquo complex

Cis-[PtI$_2$(n-C$_3$H$_7$NH$_2$)$_2$] (127 g, 0.22 mol) was slurried with a warm (50° C.) solution of silver nitrate (73 g, 0.43 mol) in 130 mls of water. The mixture was stirred for 4 hours during which time the yellow suspension turned dark grey. The mixture was then treated with charcoal, stirred and filtered through a porosity 4 sinter. The residue was triturated with water (20 mls) and the filtrates combined to give a clear orange solution (total volume 150 mls). The addition of a crystal of NaCl gave no precipitate of AgCl which indicated that the solution was silver-free. The solution was treated with charcoal and filtered through a porosity 4 sinter immediately before use as there was a tendency for the pale yellow solution to darken owing to slow decomposition to platinum.

EXAMPLE 3

Preparation of the n-pentylamine diaquo complex cis-[PtI$_2$(n—C$_5$H$_{11}$NH$_2$)$_2$] (86 g, 0.14 mol) was slurried with a warm (50° C.) solution of silver nitrate (43.8 g, 0.27 mol) in 100 mls of water and 80 mls of ethanol. The mixture was stirred overnight, and then stirred with charcoal. The solids were filtered off on a porosity 4 sinter to give a cloudy orange solution. This cloudiness persisted despite several filtrations through porosity 4 sinters.

EXAMPLE 4

Cis-bis(chloroacetato) bis(n-propylamine)platinum II, cis-[PtClCH$_2$CO$_2$)$_2$(n-C$_3$H$_7$NH$_2$)$_2$]

An aqueous solution of the n-propylamine diaquo complex (37 mls, 0.054 mol) was added to a warm, stirred solution of potassium chloroacetate, prepared from chloroacetic acid (15 g, 0.16 mol) and potassium hydroxide (9 g, 0.16 mol) in 100 mls of water. A dark, oily solid formed which changed to a more brittle solid on standing (60 hours). The pale yellow brown solid was filtered off on a porosity 3 sinter, washed well with water and dried in vacuo at 50° C.

Crude yield = 14.3 g (54%).

The crude produce (14.3 g) was dissolved in 125 mls of boiling ethanol. The solution was stirred with charcoal, filtered while hot through a porosity 4 sinter and allowed to cool. A white crystalline solid was formed.

Yield = 6.4 g (overall yield = 24%).

| Elemental analysis | | | | | |
|---|---|---|---|---|---|
| | Pt | C | H | N | O | Cl |
| Calculated % | 39.0 | 24.0 | 4.4 | 5.6 | 12.8 | 14.2 |
| Found % | — | 23.8 | 4.4 | 5.5 | — | — |

EXAMPLE 5

Cis-bis(bromoacetato)bis(n-propylamine)platinum(II), cis-[Pt(BrCH$_2$CO$_2$)$_2$(n-C$_3$H$_7$NH$_2$)$_2$]

Bromoacetic acid (5 g, 0.04 mol) was added to an aqueous solution of the n-propylamine diaquo complex (26 ml, 0.01 mol). A concentrated aqueous solution of sodium hydroxide was then added to the stirred solution until the pH had increased to 6-7. This gave an oil which transformed to a solid on standing overnight. The solid was then filtered off on a porosity 3 sinter, washed well with water and dried by suction.

Crude yield = 1.5 g (25%).

The crude bromoacetato complex was rather inefficiently recrystallized from 5 ml of hot ethanol, which gave pale yellow crystals.

Yield = 0.1 g (overall yield = 2%).

| Elemental Analysis | | | | | |
|---|---|---|---|---|---|
| | Pt | C | H | N | O | Br |
| Calculated % | 33.1 | 20.4 | 3.8 | 4.8 | 10.9 | 27.1 |
| Found % | — | 19.4 | 3.6 | 4.8 | — | — |

Infra-red Spectrum

The nitrogen-hydrogen stretching modes ($v_{N-H}$) occur at 3190, 3150 and 3110 cm$^{-1}$ and there is a bromoacetate absorption at 1615 cm$^{-1}$ ($v_{C=O}$).

EXAMPLE 6

Cis-bis (n-butylamine) bis(chloroacetato) platinum (II), cis-[Pt(ClCH$_2$CO$_2$)$_2$(n-C$_4$H$_9$NH$_2$)$_2$]

A solution of potassium chloroacetate in 100 mls of water, prepared from chloroacetic acid (21.6 g, 0.14 mol) was added to a solution of the n-butylamine diaquo complex in water (76 mls, 0.046 mol). A blue solution was formed immediately in which a dark blue-green oil settled. A white suspension was also observed. The mixture was allowed to stand for 60 hours and then the solids were filtered off on a porosity 3 sinter, washed well with water and air dried. The solid was then crushed in a mortar, washed with diethyl ether and dried in vacuo at 60° C. The crude product was pale green.

Crude yield = 11.1 g (42%).

The crude product (9.6 g) was dissolved in 50-60 mls of hot ethanol. The orange solution was stirred with charcoal and filtered while hot through a porosity 4 sinter. White acicular crystals formed on cooling the filtrate which was subsequently chilled at 5° C. overnight. The crystals filtered off on a porosity 3 sinter and washed twice with ethanol, causing them to effloresce to a white powder, which was dried in vacuo at 40° C.

Yield—3.3 g (overall yield = 12.6%).

| Elemental Analysis | | | | | |
|---|---|---|---|---|---|
| | Pt | C | H | N | O | Cl |
| Calculated % | 36.9 | 27.3 | 5.0 | 5.3 | 12.1 | 13.4 |
| Found % | — | 26.9 | 5.0 | 5.3 | — | — |

Infra-red Spectrum

The nitrogen-hydrogen stretching modes ($v_{N-H}$) occur at 3195 and 3130 cm$^{-1}$ and there is a chloroacetate absorption at 1650 cm$^{-1}$ ($v_{C=O}$).

EXAMPLE 7

Aquobis(n-butylamine)sulphatoplatinum(II), [Pt(SO$_4$)(H$_2$O)(n—C$_4$H$_9$NH$_2$)$_2$]

Concentrated sulphuric acid (7 ml, 0.13 mol) was added to a chilled, stirred solution (42 ml) of the n-butylamine diaquo complex (0.024 mol). After storage at 5° C. for 3 days white chrstals appeared, which were filtered off on a porosity 3 sinter and washed with water. The crystals effloresced on washing to form a white powder, which was dried in vacuo at 50° C.

Crude yield = 2.1 g (19%).

The complex was insoluble in hot water, ethanol, aqueous sodium sulphate solution, methanol and acetone. However, the complex was soluble in concentrated sulphuric acid and was recrystallised as follows.

The crude sulphato complex (0.8 g) was dissolved in 1 ml of warm concentrated sulphuric acid on a porosity 4 sintered glass filter. The yellow solution so formed was then drawn through by suction into a receiver flask containing ice-cold water (2 ml). This gave a white precipitate which was filtered off, washed with ethanol and dried in vacuo.

Yield = 0.4 g (overall yield = 9.5%).

| Elemental Analysis | | | | | | |
|---|---|---|---|---|---|---|
| | Pt | C | H | N | O | S |
| Calculated % | 42.8 | 21.1 | 5.3 | 6.2 | 17.6 | 7.0 |
| Found % | — | 20.8 | 5.2 | 6.1 | — | — |

Infra-red Spectrum

The nitrogen-hydrogen stretching modes ($\nu_{N-H}$) occur at 3220 and 3120 cm$^{-1}$ and there are sulphate absorptions at 1170, 1115, 1030 and 940 cm$^{-1}$.

EXAMPLE 8

Bis (n-butylamine)oxalatoplatinum(II), [Pt(C$_2$O$_4$)(n—C$_4$H$_9$NH$_2$)$_2$]

A solution of the n-butylamine diaquo complex (37 ml, 0.024 mol) was added to a warm stirred solution of potassium oxalate (13 g, monohydrate, 0.07 mol) in 40 ml of water. The white precipitate so formed was stirred for 30 minutes, filtered off on a porosity 4 sinter, washed with water and dried in vacuo at 50° C.

Crude yield = 5.4 g (50%).

The crude oxalto complex was recrystallised as follows. The product was added to a stirred, vigorously boiling aqueous solution of 0.1 M potassium oxalate (800 ml). The solution was boiled for 30 minutes to effect dissolution during which time the solution darkened owing to some platinum formation. The solution was then treated with charcoal, stirred, cooled to 80° C. and filtered through a porosity 4 sinter. White crystals formed on cooling the filtrate to 25° C. and after storage for 3 days at 5° C., the product was filtered off, washed with water and air dried.

Yield 0.2 g (2%).

The low yield is due to instability of the product in boiling 0.1 M potassium oxalate.

| Elemental Analysis | | | | | |
|---|---|---|---|---|---|
| | Pt | C | H | N | O |
| Calculated % | 45.4 | 28.0 | 5.2 | 6.5 | 14.9 |
| Found % | — | 27.2 | 5.1 | 6.3 | — |

Infra-red Spectrum

The nitrogen-hydrogen stretching modes ($\nu_{N-H}$) occur at 3200 and 3110 cm$^{-1}$ and there are oxalate absorptions at 1695 and 1669 cm$^{-1}$ due to the carbonyl stretching vibrations ($\nu_{C=O}$). The spectra of the crude iso- and n-butylamine oxalato complexes showed strong peaks at 775 and 1300 cm$^{-1}$. These peaks were absent from the spectra of the recrystallised compounds.

EXAMPLE 9

Oxalatobis(n-propylamine)platinum(II) [Pt(C$_2$O$_4$)(n-C$_3$H$_7$NH$_2$)$_2$]

A warm saturated aqueous solution of potassium oxalate (38 g, monohydrate, 0.20 mol) was added to a solution of the n-propylamine diaquo complex (120 g, 0.04 mol). The white precipitate so obtained was stirred for 1 hour at 50° C., filtered off on a porosity 3 sinter, washed with water and dried in vacuo.

Crude yield = 10.8 g (67%).

The crude product (5.8 g) was dissolved in a vigorously boiling solution of K$_2$C$_2$O$_4$.H$_2$O (13 g, 0.07 mol) in 700 mls of water. The clear pale yellow solution formed was treated with charcoal, stirred, cooled to 80° C., filtered through a porosity 4 sinter and allowed to cool to 25° C. during which time crystallisation occured. The mixture was chilled at 5° C. overnight and the crystals were filtered off on a porosity 3 sinter, washed with water and dried in vacuo.

Yield = 48% (based on crude produce).

| Elemental analysis | | | | | |
|---|---|---|---|---|---|
| | Pt | C | H | N | O |
| Calculated % | 48.6 | 23.9 | 4.5 | 7.0 | 16.0 |
| Found % | — | 23.5 | 4.5 | 6.8 | — |

Infra-red spectrum

The nitrogen-hydrogen stretching modes ($\nu_{N-H}$) occur at 3250 and 3150 cm$^{-1}$ and there are oxalate absorptions at 1695, 1680 and 1655 cm$^{-1}$ due to the carbonyl stretching vibrations ($\nu_{C=O}$).

EXAMPLE 10 cis-aquabis(n-butylamine)sulphato platinum (II) cis-[Pt(SO$_4$)(H$_2$O)(n-C$_4$H$_9$NH$_2$)$_2$]

Concentrated sulphuric acid (26 ml, 0.49 mole) was added dropwise to a stirred aqueous solution of n-butylamine diaquo complex (43 ml, 0.049 mole) after cooling to 5° C. The solution, after storing overnight at room temperature, deposited a white precipitate, which was filtered off on a porosity 3 sinter, washed successively with a small amount of cold water and ethanol and dried in vacuo at 60° C. Yield of crude product = 3 g.

| Assay: | | | | | | |
|---|---|---|---|---|---|---|
| | Pt | C | H | N | O | S |
| Calculated % | 42.8 | 21.1 | 5.3 | 6.2 | 17.6 | 7.0 |
| Found % | — | 21.0 | 5.0 | 6.5 | — | — |

Infra-red spectrum

The $\nu_{N-H}$ modes occur at 3210 and 3140 cm$^{-1}$, sulphate absorbs at 1127 and 1106, 1021 and 936 cm$^{-1}$, and water absorptions occur at 1609 and 3500 cm$^{-1}$.

EXAMPLE 11

Preparation of cis-aquabis(n-propylamine)sulphato platinum(II) cis-[Pt(SO$_4$)(H$_2$O)(n-C$_3$H$_7$NH$_2$)$_2$]

The n-propylamine diaquo complex (0.068 mole, assuming 100% conversion) was cooled to 5° C. and concentrated sulphuric acid (37 ml, 0.68 mole) was added dropwise so that the temperature of the solution did not rise above 20° C. After addition of H$_2$SO$_4$ was complete the solution was stirred for an hour during which time a small amount (0.5 g) of a white solid precipitated. After filtration the filtrate was allowed to stand for 5 days and some white needles separated. These were filtered off on a porosity 3 sinter, washed with ice cold water and ethanol and dried in vacuo at 80° C.

Yield = 4.6 g (15%).

| Assay: | Pt | C | H | N | O | S |
|---|---|---|---|---|---|---|
| Calculated % | 45.64 | 16.86 | 4.72 | 6.55 | 18.72 | 7.50 |
| Found % | — | 17.12 | 4.19 | 6.16 | — | — |

Infra-red spectrum $\nu_{N-H}$ occurs at 3220 and 3130 cm$^{-1}$, sulphate absorptions are found at 1230, 1110, 1010 and 993 cm$^{-1}$, water absorptions occur at 1595 and 3500 cm$^{-1}$.

EXAMPLE 12

Oxalatobis(n-pentylamine)platinum(II)
[Pt(C$_2$O$_4$)(n—C$_5$H$_{11}$NH$_2$)$_2$]

A solution of the n-pentylamine diaquo complex (45 mls, 0.035 mol) in aqueous ethanol was added to a solution of K$_2$C$_2$O$_4$.H$_2$O (32 g, 0.17 mol) in 100 mls of water, to form a fine white precipitate after 5–10 seconds. The mixture was stirred for 30 minutes and the product filtered off on a porosity 3 winter, washed well with hot water and dried in vacuo at 60° C.

Crude yield = 5.8 g (36%).

The complex was recrystallised from hot ethanol without apparent decomposition i.e. the crude product (2.8 g) was dissolved in approx. 150 mls of boiling ethanol. The solution was concentrated to a volume of 30–40 mls, treated with charcoal and filtered through a porosity 4 sinter. A white solid formed when the solution was cool. This was filtered off on a porosity 3 sinter. More white solid was obtained when an equal volume of water was added to the ethanolic filtrate. The purified products were combined, washed with water, ethanol and dried in vacuo.

Yield = 1.7 g (overall yield = 22%).

| Elemental Analysis [Pt(C$_2$O$_4$)(n-C$_5$H$_{11}$NH$_2$)] | Pt | C | H | N | O |
|---|---|---|---|---|---|
| Calculated % | 42.7 | 31.5 | 5.6 | 6.2 | 14.0 |
| Found % | — | 31.8 | 5.6 | 6.2 | — |

Intra-red spectrum

The nitrogen-hydrogen stretching modes ($\nu_{N-H}$) occur at 3200 and 3110 cm$^{-1}$ and there are oxalate absorption at 1693 and 1667 cm$^{-1}$ due to the carbonyl stretching vibration ($\nu_{C=O}$).

EXAMPLE 13

Cis-bis(chloroacetato) bis(n-pentylamine)platinum(II),
cis-[Pt(ClCH$_2$CO$_2$)$_2$(n-C$_5$H$_{11}$NH$_2$)$_2$]

A solution of potassium chloroacetate, prepared from chloroacetic acid (19.7 g, 0.21 mol) and potassium hydroxide (11.8 g, 0.21 mol) in 100 mls of water, was added to a solution of the n-pentylamine diaquo complex (0.07 mol) in aqueous ethanol (90 mls) at 25° C. This gave a brown oil. The mixture was stirred for 30 minutes and allowed to stand for 60 hours during which time the oil hardened to a brown solid. The solid was filtered off on a porosity 3 sinter, washed well with water, air dried, washed with diethyl ether and then dried in vacuo at 60° C.

Crude yield = 14.0 g (36%).

The crude product (8 g) was added to 30 mls of boiling ethanol. The brown solution was stirred with charcoal, filtered hot through a porosity 4 sinter and allowed to cool. This gave a white solid which was filtered off through a porosity 3 sinter, and washed with ethanol.

Yield = 4.8 g (overall yield = 22%).

| Elemental analysis | Pt | C | H | N | O | Cl |
|---|---|---|---|---|---|---|
| Calculated % | 35.1 | 30.2 | 5.4 | 5.0 | 11.5 | 12.7 |
| Found % | — | 29.9 | 5.5 | 5.0 | — | — |

Infra-red spectrum

The nitrogen-hydrogen stretching modes ($\nu_{N-H}$) occur at 3200, 3160 and 3110 cm$^{-1}$ and there are chloroacetate absorptions at 1600 cm$^{-1}$ owing to the carbonyl stretching vibrations.

EXAMPLE 14 cis-[PtCl$_2$(n—C$_3$H$_7$NH$_2$)$_2$]

Concentrated hydrochloric acid (50 ml.) was added to a solution of the n-propylamine diaquo complex and stirred at 40° C. for two hours. The slurry of crude product was cooled overnight, filtered and the residue washed with water ethanol and dried in vacuo. The crude product was recrystallised from NN dimethylformamide (500 ml) by addition of 1 liter of 0.1 N hydrochloric acid.

Yield: 36.7 g, 80% (based on 64 g [PtI$_2$A$_2$]).
IR$\nu$ Pt-Cl 320 cm$^{-1}$.

EXAMPLE 15 cis-[PtCl$_2$(n—C$_4$H$_9$NH$_2$)$_2$]

This complex was prepared in an identical manner to that described in Example 14.

Yield = 62%.

EXAMPLE 16 cis-dichlorobis(1-aminopentane)platinum(II)

n-amylamine (0.70 g; 8 m.mol) was added to a solution of K$_2$PtCl$_4$ (1.66 g; 4 m.mol) in water (15 ml) and sufficient methanol (5 ml) was added in order to produce a homogeneous solution. The reaction mixture was left overnight and the pale yellow solid that separated was filtered off, and washed successively with hot, 6 M hydrochloric acid, water, acetone, methanol, and ether.

| Analysis: | C | H | N |
|---|---|---|---|
| Calculated % | 27.3 | 5.95 | 6.4 |
| Found % | 27.0 | 5.80 | 6.3 |

The following complexes were prepared in a similar way:
cis-dichlorobis(1-aminohexane)platinum(II)
cis-dichlorobis(1-aminoheptane)platinum(II)
cis-dichlorobis(2-aminoheptane)platinum(II)
cis-dichlorobis(1-aminooctane)platinum(II)

Clinical Testing Data

Complexes according to the invention were tested for antitumour activity against L-1210 leukaemia, ADJ/PC6A tumour or S180 solid tumour in mice. In the results which follow, dosages are quoted in mg/Kg body weight and the evaluation of effectiveness (% T/C) against L1210 is calculated as the median survival time of treated mice divided by the median survival time of untreated (control) mice expressed as a percentage. Thus a % T/C of 100 indicates no activity and a % T/C of greater than or equal to 125 is considered to be indicative of significant antitumour activity.

Against a solid tumour, the % T/C is a measure of tumour regression and is the percentage of tumour weight in treated mice to that in control mice. Against ADJ/PC6A and S180, several dose levels were given and ranged from lethal to non-tumour inhibitory, allowing the calculation of $LD_{50}$ and $ID_{90}$ (minimum dose to cause 90% tumour inhibition) in one experiment. The ratio $LD_{50}/ID_{90}$ is the therapeutic index and is a measure of the selectivity of the compound as an antitumour agent. All compounds were administered intraperitoneally as a single dose suspended in arachis oil.

| Bis(n-propylamino)bis(chloroacetato)platinum(II) | | |
|---|---|---|
| L1210 | Single dose | @ 12 mg/Kg % T/C = 167 |
| | | @ 24 mg/Kg 5 T/C = 167 |
| | Daily dose for 9 days | @ 6 mg/Kg % T/C = 225 |

| Bis-(n-propylamino)oxalatoplatinum(II) | | |
|---|---|---|
| L1210 | Single dose | @ 59 mg/Kg % T/C = 129 |
| | Daily dose for 9 days | @ 15 mg/Kg % T/C = 143 |
| | | @ 30 mg/Kg % T/C = 143 |

| Bis-(n-butylamine)-bis-(chloroacetato)platinum(II) | | |
|---|---|---|
| L1210 | Single dose | @ 256 mg/Kg % T/C = 107 |
| | Daily dose for 9 days | @ 32 mg/kg % T/C = 136 |

| Bis-(ethylamine)oxalatoplatinum(II) | | | |
|---|---|---|---|
| ADJ/PC6A | $ID_{90}$= 3.9 | $LD_{50}$= 38 | TI = 0.7 |
| S180 (carrier water) | | T/C = 21% @ 10 mg/Kg | |

| Cis-bis(n-propylamine)dichloroplatinum(II) | | | |
|---|---|---|---|
| ADJ/PC5A | $ID_{90}$ = <12 | $LD_{50}$= 26.5 | TI = =>2.2 |
| L1210 | Single dose | @ 8 mg/Kg % T/C = 157 | |
| | Daily dose for 9 days | @ 4 mg/kg % T/C = 157 | |

| Cis-bis-(n-butylamine)dichloroplatinum(II) | | | |
|---|---|---|---|
| ADJ/PC6A | $ID_{90}$= <10 | $LD_{50}$ = 110 | TI = >11 |

| Cis-bis-(n-pentylamine)dichloroplatinum(II) | | | |
|---|---|---|---|
| ADJ/PC6A | $ID_{90}$ = 37 | $LD_{50}$ = 92 | TI = 2.5 |

We claim:

1. A cis-coordination compound of platinum having the structure:

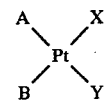

in which X and Y are the same or different ligands selected from sulphate, phosphate, nitrate, oxalate, halogen-substituted acetate and water or together form a dicarboxylate ligand selected from the group consisting of succinato, glutarato, adipato, pimelato, malato and phthalato ligands and A and B are the same or different straight-chain aliphatic amines selected from the group consisting of n-propylamine, n-butylamine and n-pentylamine coordinated to the Pt through their N atoms, such that the platinum is present as $Pt^{2+}$.

2. A compound according to claim 1 wherein the phosphate is in the form of $H_2PO_4^-$ or $HPO_4^{2-}$.

3. A compound according to claim 1 wherein the dicarboxylate ligand is selected from the group consisting of succinato, glutarato, adipato, pimelato, malato and phthalato ligands.

4. A compound according to claim 1 selected from the group consisting of:
cis-Pt(ClCH$_2$CO$_2$)$_2$(n—C$_3$H$_7$NH$_2$)$_2$;
cis-Pt(BrCH$_2$CO$_2$)$_2$(n—C$_3$H$_7$NH$_2$)$_2$;
cis-Pt(ClCH$_2$CO$_2$)$_2$(n—C$_4$H$_9$NH$_2$)$_2$;
Pt(SO$_4$)(H$_2$O)(n—C$_4$H$_9$NH$_2$)$_2$;
Pt(C$_2$O$_4$)(n—C$_4$H$_9$NH$_2$)$_2$;
Pt(C$_2$O$_4$)(n—C$_3$H$_7$NH$_2$)$_2$;
cis-Pt(SO$_4$)(H$_2$O)(n—C$_4$H$_9$NH$_2$)$_2$;
cis-Pt(SO$_4$)(H$_2$O)(n—C$_3$H$_7$NH$_2$)$_2$;
Pt(C$_2$O$_4$)(n—C$_5$H$_{11}$NH$_2$)$_2$; and
cis-Pt(ClCH$_2$CO$_2$)$_2$(n—C$_5$H$_{11}$NH$_2$)$_2$.

* * * * *